US007381703B2

(12) United States Patent
Bertino et al.

(10) Patent No.: US 7,381,703 B2
(45) Date of Patent: Jun. 3, 2008

(54) APLIDINE FOR MULTIPLE MYELOMA TREATMENT

(75) Inventors: Joseph R. Bertino, Branford, CT (US); Daniel Medina, Hampton, NJ (US); Glynn Thomas Faircloth, Cambridge, MA (US); Constantine S. Mitsiades, Boston, MA (US); Kenneth Anderson, Wallesley, MA (US); Nicholas Mitsiades, West Roxbury, MA (US)

(73) Assignees: Dana-Faber Cancer Institute, Inc., Boston, MA (US); Pharma Mar, S.A., Madrid (ES)

( * ) Notice: Subject to any disclaimer, the term of this patent is extended or adjusted under 35 U.S.C. 154(b) by 0 days.

(21) Appl. No.: 10/548,710

(22) PCT Filed: Mar. 12, 2004

(86) PCT No.: PCT/GB2004/001062

§ 371 (c)(1),
(2), (4) Date: Apr. 11, 2006

(87) PCT Pub. No.: WO2004/080477

PCT Pub. Date: Sep. 23, 2004

(65) Prior Publication Data

US 2006/0172926 A1 Aug. 3, 2006
US 2007/0149445 A9 Jun. 28, 2007

Related U.S. Application Data

(60) Provisional application No. 60/520,293, filed on Nov. 14, 2003, provisional application No. 60/454,125, filed on Mar. 12, 2003.

(51) Int. Cl.
*A61K 38/15* (2006.01)
*A61P 35/00* (2006.01)

(52) U.S. Cl. ....................................................... 514/11
(58) Field of Classification Search ...................... None
See application file for complete search history.

(56) References Cited

U.S. PATENT DOCUMENTS

| 4,493,796 A | 1/1985 | Rinehart, Jr. |
| 4,670,262 A | 6/1987 | Battelli et al. |
| 5,294,603 A | 3/1994 | Rinehart |
| 5,462,726 A | 10/1995 | Lodge |
| 5,573,781 A | 11/1996 | Brown et al. |
| 5,834,586 A | 11/1998 | Rinehart et al. |
| 5,883,135 A | 3/1999 | Gyory et al. |
| 6,030,943 A | 2/2000 | Crumb et al. |
| 6,034,058 A | 3/2000 | Rinehart et al. |
| 6,080,877 A | 6/2000 | Swindell et al. |
| 6,153,731 A | 11/2000 | Rinehart et al. |
| 6,156,724 A | 12/2000 | Rinehart et al. |
| 6,509,315 B1 | 1/2003 | Joullié et al. |
| 6,610,699 B2 | 8/2003 | Cavazza et al. |
| 6,710,029 B1 | 3/2004 | Rinehart et al. |
| 6,890,904 B1 | 5/2005 | Wallner et al. |
| 7,064,105 B2 | 6/2006 | Joullie et al. |
| 2001/0021380 A1* | 9/2001 | Pluenneke ............... 424/131.1 |
| 2002/0098185 A1* | 7/2002 | Sims et al. ............... 424/145.1 |
| 2003/0044893 A1* | 3/2003 | Baum et al. ............... 435/69.1 |

FOREIGN PATENT DOCUMENTS

| EP | 0 048 149 A1 | 3/1982 |
| EP | 0 393 883 | 10/1990 |
| ES | 2 102 322 | 7/1997 |
| WO | WO 91/04985 | 4/1991 |
| WO | WO 93/00362 | 1/1993 |
| WO | WO 98/01352 | 1/1998 |
| WO | WO 98/17275 | 4/1998 |
| WO | WO 98/17302 | 4/1998 |
| WO | WO 99/42125 | 8/1999 |
| WO | WO 00/06134 | 2/2000 |
| WO | WO 00/71135 | 11/2000 |
| WO | WO 01/35974 A2 | 5/2001 |
| WO | WO 01/76616 A1 | 10/2001 |
| WO | WO 02/02596 A2 | 1/2002 |
| WO | WO 02/030441 A2 | 4/2002 |
| WO | WO 03/033013 A1 | 4/2003 |
| WO | WO 2004/080421 A2 | 9/2004 |

OTHER PUBLICATIONS

Mitsiades et al. Pre-clinical studies in support of the clinical development of Aplidin® (APL) for the treament of multiple myeloma (MM). Blood. Nov. 16, 2003, vol. 102, No. 11, p. 74a, Abstract# 250.*
Ady-Vago, N. et al., "L-Carnitine as a protector Against Aplidine Induced Skeletal Muscle Toxicity," *Proceedings of the American Association for Cancer Research*, 42:545 (2001).
Bergeron, Raymond J. et al., "Antineoplastic and Antiherpetic Activity of Spermidine Catecholamide Iron Chelators," *Biochemical and Biophysical Research Communications*, 121(3):848-854 (1984).
Broggini, M. et al., "Aplidine Blocks VEGF Secretion and VEGF/VEGF-RI Autocrine Loop in a Human Leukemic Cell Line," *11th NCI-EORTC-AACR on New Drugs in Cancer Therapy*, Amsterdam (2000), Abstract 214.
Chapa, A.M. et al., "Influence of Intravenous L-Carnitine Administration in Sheep Preceding an Oral Urea Drench$^{1,2}$," *Journal of Animal Science*, 76(11):2930-2937 (1998).
Chauhan, D. et al., "Multiple Myeloma Cell Adhesion-Induced Interleukin-6 Expression in Bone Marrow Stromal Cells Involves Activation of NF-κB," *Blood*, 87(3):1104-1112 (1996).
Depenbrock, H. et al., "In Vitro Activity of Aplidine, a New Marine-Derived Anti-Cancer Compound, on Freshly Explanted Clonogenic Human Tumour Cells and Haematopoietic Precursor Cells," *British Journal of Cancer*, 78(6):739-744 (1998).
"Didemnin B," *Drugs of the Future*, 20(1):77 (1995).
Erba, E. et al., "Cell Cycle Phases Perturbations Induced by New Natural Marine Compounds," *Annals of Oncology*, 7 (Suppl. 1)(283):82 (1996).

(Continued)

*Primary Examiner*—Jeffrey Edwin Russel
(74) *Attorney, Agent, or Firm*—Fish & Richardson P.C.

(57) ABSTRACT

Aplidine and aplidine analogues are used in the manufacture of a medicament for treating multiple myeloma.

3 Claims, 7 Drawing Sheets

OTHER PUBLICATIONS

Faircloth, G. et al., "Aplidine (APL) is a Novel Marine-Derived Depsipeptide with in Vivo Antitumor Activity," *Proceedings of the American Association for Cancer Research*, 39(1551):227 (1998).

Faircloth, G. et al., "Dehydrodidemnin B (DDB) a New Marine Derived Anti-Cancer Agent (MDA) with Activity Against Experimental Tumor Models"and "Biological Activity of Thiocoraline. A New Depsipeptide from a Marine Micromonospora," *Annals of Oncology*, 7 (Suppl. 1)(111 and 112):34 (1996).

Faircloth, G. et al., "Marine (MA) Depsipeptides (DEP) with Activity (A) against Solid Tumours (ST) Models," *Proceedings 8th ECCO Congress*, 31A (Suppl. 5):S29, Abstract No. 122 (1995).

Faircloth, G. et al., "Preclinical Characterization of Aplidine (APD), a New Marine Anticancer Depsipeptice (MADEP)," *Proceedings of the American Association for Cancer Research*, 38(692):103 (1997).

Faircloth, G. et al., "Preclinical Development of Aplidine, a Novel Marine-Derived Agent with Potent Antitumor Activity," *Annals of Oncology*, 9 (Suppl. 2):34, Abstract No. 129 (1998).

Faircloth, G. et al., "Schedule-Dependency of Aplidine, a Marine Depsipeptide with Antitumor Activity," *Proceedings of the American Association for Cancer Research*, 40 (2612):394-395 (1999).

Geldof, Albert A. et al., "Cytotoxicity and Neurocytotoxicity of New Marine Anticancer Agents Evaluated Using in Vitro Assays," *Cancer Chemother, Pharmacol.*, 44:312-318 (1999).

Genin, Michael J. et al., "Synthesis and Crystal Structure of a Peptidomimetic Containing the (R)-4, 4-Spiro Lactam Type-II β-Turn Mimic," *Journal of Organic Chemistry*, 58(8):2334-2337 (1993).

Giovanella, B.C. et al., "Correlation Between Response to Chemotherapy of Human Tumors in Patients and in Nude Mice," *Cancer*, 52(7):1146-1152 (1983).

Gomez-Fabre, P.M. et al., "Polamine Contents of Human Breast Cancer Cells Treated with the Cytotoxic Agents Chlorpheniramine and Dehydrodidemnin B," *Cancer Letters*, 113 (1 and 2): 141-144 (1997).

Hideshima, T. et al., "The Proteasome Inhibitor PS-341 Inhibits Growth, Induces Apoptosis, and Overcomes Drug Resistance in Human Multiple Myeloma Cells," *Cancer Res.*, 61:3071-3076 (2001).

Jimeno et al., "A Correlation of Selective Antitumor Activities of the Marine-Derived Compound Aplidine Using Different Models," *10th NCI-EORTC-AACR Symposium on Molecular Targets and Cancer Therapeutics*, Washington (1999), Abstract 311.

Jimeno, J. et al., "Translational Studies Supporting the Clinical Development of Aplidine (APL) in Pediatric Leukemia," *Annals of Oncology*, 13 (Suppl. 5):19, Abstract No. 65P (2002).

Jou, Gemma et al., "Total Synthesis of Dehydrodidemnin B. Use of Uronium and Phosphonium Salt Coupling Reagents in Peptide Synthesis in Solution," *Journal of Organic Chemistry*, 62(2):354-366 (1997);

Lobo, C. et al., "Effect of Dehydrodidemnin B on Human Colon Carcinoma Cell Lines," *Anticancer Research*, 17(1A):333-336 (1997).

Luber-Narod, J. et al., "In Vitro Safety Profile of Aplidine, A Marine Natural Product with Chemotherapeutic Potential," *Proceedings of the AACR*, 42, Abstract 374 (2001).

Mastbergen, S.C. et al., "Cytotoxicity and Neurocytotoxicity of Aplidine, a New Marine Anticancer Agent Evaluated Using in Vitro Assays," *Annals of Oncology*, 9 (Suppl. 2)(131) (1998).

Mayer, S.C. et al., "Synthesis of New Didemnin B Analogs for Investigations of Structure/Biological Activity Relationships," *J. Org. Chem.*, 59(18):5192-5205 (1994).

Mitsiades, C.S. et al., "Activation of NF-kappaB and Upregulation of Intracellular Anti-Apoptotic Proteins via the IGF-1/Akt Signaling in Human Multiple Myeloma Cells: Therapeutic Implications," *Oncogene*, 21(37):5673-5683 (2002).

Mitsiades, C.S. et al., "TRAIL/Apo2L Ligand Selectively Induces Apoptosis and Overcomes Drug Resistance in Multiple Myeloma: Therapeutic Applications," *Blood*, 98(3):795-804 (2001).

Mitsiades, N. et al., "Molecular Sequelae of Histone Deacetylase Inhibition in Human Malignant B Cells," *Blood*, 101(10):4055-4062 (2003).

Mitsiades, N. et al., "Molecular Sequelae of Proteasome Inhibition in Human Multiple Myeloma Cells," *Proc Natl Acad Sci USA*, 99(22):14374-14379 (2002).

Mitsiades, N. et al., "The Proteasome Inhibitor PS-341 Potentiates Sensitivity of Multiple Myeloma Cells to Conventional Chemotherapeutic Agents: Therapeutic Applications," *Blood*, 101(6):2377-2380 (2003).

Montgomery, D.W. et al., "Didemnin B Alters the Specific Binding of Prolactin to Human Lymphocytes and Decreases the Circulating Level of Prolactin in Mice," *Federal Proceedings*, 44(3):634, #1311 (1985).

Montgomery, David W. et al., "Didemnin B: A New Immunosuppressive Cyclic Peptide with Potent Activity In Vitro and In Vivo[1] ," *Transplantation*, 40(1);49-56 (1985).

Nuijen, B. et al., "Pharmaceutical Development of Anticancer Agents Derived from Marine Sources," *Anti-Cancer Drugs*, 11:793-811 (2000).

Palangie, T. et al., "Dose-Intense Salvage Therapy After Neoadjuvant Chemotherapy: Feasibility and Preliminary Results," *Cancer Chemother: Pharmacol.*, 44 (Suppl.):S24-S25 (1999).

Raymond, Eric et al., "Preliminary Results of a Phase I and Pharmacokinetic Study of Aplidine Given as a 24-hour Infusion Every 2 Weeks in Patients With Solid Tumors and Non Hodgkin's Lymphomas," *Proceedings of the American Association for Cancer Research*, 41(3886) (2000).

Rinehart, K., "Didemnin and its Biological Properties," *Escom.*, pp. 626-631 (1987).

Rinehart, Kenneth L. et al., "Biologically Active Peptides and Their Mass Spectra," *Pure and Applied Chemistry*, 54(12):2409-2424 (1982).

Rinehart, Kenneth L. et al., "Didemnins and Tunichlorin: Novel Natural Products from the Marine Tunicate Trididemnum Solidum[1]," *Journal of Natural Products*, 51(1):1-21 (1988).

Rinehart, Kenneth L. et al., "Total Synthesis of Didemnins A, B and C[1,2]," *Journal of the American Chemical Society*, 109(22):6846-6848 (1987).

Rinehart, Kenneth L., Jr. et al., "Antiviral and Antitumor Compounds from Tunicates[1,2]" *Federation Proceedings*, 42(1):87-90 (1983).

Rinehart, Kenneth L., Jr. et al., "Didemnins: Antiviral and Antitumor Depsipeptides from a Caribbean Tunicate," *Science*, 212(4497):933-935 (1981).

Rinehart, Kenneth L., Jr. et al., "Structure of the Didemnins, Antiviral and Cytotoxic Depsipeptides from a Caribbean Tunicate[1]," *Journal of the American Chemistry Society*, 103(7):1857-1859 (1981).

Sakai, Ryuichi et al., "Structure—Activity Relationships of the Didemnins [1,2]," *Journal of Medicinal Chemistry*, 39(14):2819-2834 (1996).

Seebach, Dieter et al., "Alkylation of Amino Acids without Loss of the Optical Activity: Preparation of α-Substituted Proline Derivatives. A Case of Self-Reproduction of Chirality[1,2]," *Journal of the American Chemical Society*, 105(16):5390-5398 (1983).

Uchiyama, H. et al., "Adhesion of Human Myeloma-Derived Cell Lines to Bone Marrow Stromal Cells Stimulates Interleukin-6 Secretion," *Blood*, 82(12):3712-3720 (1993).

Urdiales, Jose L. et al., "Antiproliferative Effect of Dehydrodidemnin B (DDB), a Depsipeptide Isolated from Mediterranean Tunicates," *Cancer Letters*, 102(1 and 2):31-37 (1996).

Vervoort, Helene et al., "Tamandarins A and B: New Cytotoxic Depsipeptides from a Brazilian Ascidian of the Family Didemnidae," *The Journal of Organic Chemistry*, 65(3):782-792 (2000).

Weiss, R. et al., "A Phase II Trial of Didemnin B in Myeloma," *Investigational New Drugs*, 12(1):41-43 (1994).

Tang et al., "Review and prospect for study of marine antitumor substances", Pharm Care & Res, vol. 1, 2002, pp. 7-16.

Office Action from corresponding Chinese application No. 2004800067241, mailed Mar. 30, 2007; translation of Office Action including translation of section 3.3 of reference AQ.

Bennett, J. Claud, and Fred Plum,eds. Cecil Textbook of Medicine, "Part XIV - Oncology", W. B. Saunders & Company, 20th Ed., vol. 1, pp. 1004-1010 (1996).

Committee for Proprietary Medicinal Products (CPMP) - "Note for Guidance on Evaluation of Anticancer Medicinal Products in Man", The European Agency for the Evaluation of Medicinal Products, EMEA, London, England, CPMP/EWP/205/95 rev. 1 corr. 14 pages, (2001).

DeVita, Jr., Vincent T, Samuel Hellman, and Steven A Rosenberg, eds. Cancer: Principles and Practice of Oncology, "Section 3 - Cancer of the Pancreas", Lippincott Williams & Wilkins, 7th Ed., 7 pages, (2005).

Draetta, Giulio et al., "Section V. Topics in Biology - Chapter 25. Cell Cycle Control and Cancer", Annual Reports in Medicinal Chemistry, pp. 241-248, 1996.

Faircloth, G. et al., "Marine (MA) Depsipeptides (DEP) with Activity (A) against Solid Tumours (ST) Models," Proceedings 8th ECCO Congress, 31A (Suppl. 5):S29, Abstract No. 122 (1995).

Hansen, Richard et al., "Continuous 5-Fluorouracil (5FU) Infusion in Carcinoma of the Pancreas: A Phase II Study", American Journal of Medical Science, 295:91-93, (1988).

Hudes et al., "Phase II trial of 96-hour paclitaxel plus oral estramustine phosphate in metastatic hormone-refractory prostate cancer", J. Clin. Oncol. 1997, 15, 3156-3163.

Kerbel, Robert S., "What is the Optimal Rodent Model for Anti-Tumor Drug Testing?", Cancer and Metasasis Reviews, 17: 301-304, (1999).

Matsuoka et al., Comparison of the effects of l-caritine, d-carnitine and scetyl-1-carnitine on the neurotoxicity of ammoniaBiochemical Pharmacology 1993, 46, 159-164.

Mead Johnson Oncology Products, Taxol (Paclitaxel) Injection Labeling Revision, Apr. 9, 1998.

O'Neil, Maryadele J., Ann Smith and Patricia E. Heckelman, eds. The Merck Index - An Encyclopedia of Chemicals, Drugs, and Biologicals, Merck & Co., Inc., 13th Ed., P. 1791, (2001).

Raymond, N. Ady-Vago et al., "25th Congress of the European Society of Medicinal Oncology", Hamburg, Germany, Oct. 13-17, 2000, reported in the Annals of Oncology, Kluwer Academic Publishers, Supplement 4 to vol. 11, Abstract 610PD, 2 pages, (2000).

Rinehart, K., Antitumor compounds from tunicates, Medical Research Reviews 2000, 20, 1-27, published online Dec. 22, 1999.

Tempero, Margaret, et al., Clinical Practice Guidlines in Oncology - v.2.2006 - "Pancreatic Adenocarcinoma" National Comprehensive Cancer Network, http://www.neen.org/professionals/physician_gls/PDF/pancreatic.pdf, 41 pages, (2006).

U.S. National Cancer Institute, U.S. National Institutes of Health, www.cancer.gov, "FactSheet", 6 pages, http://www.cancer.gov/cancertopics/factsheet/information/clinical-trials (2006).

U.S. National Cancer Institute, U.S. National Institutes of Health, www.cancer.gov., "Pancreatic Cancer (PDQ®): Treatment", 3 pages, http://www.cancer.gov/cancertopics/pdq/treatment/pancreatic/healthprofessional (2006).

U.S. National Cancer Instutite, U.S. National Institutes of Health, www.cancer.gov, "Cancer Topics - Colon and Rectal Cancer", http://www.cancer.gov/cancertopics/types/colon-rectal, 2 pages (2007).

U.S. National Cancer Institute, U.S. National Institutes of Health, www.cancer.gov., "Gastric Cancer (PDQ®): Treatment - General Information About Gastric Cancer", http://www.cancer.gov/cancertopics/pdq/treatment/gastric/patient, 4 pages (2007).

Van-Boxtel, C. J., B. Santoso and I. R. Edwards, eds. Drug Benefits and Risks: International Textbook of Clinical Pharmacology, "Drug Development", Chapter 9, pp. 91-102, (2001).

Virmani et al., "Protective actions of 1-carnitine and acetyl-1-carnitine on the neurotoxicity evokes my mitochondrial upcoupling or inhibitors", Pharmacological Research, 1995, 32, 383-389.

* cited by examiner

APLIDINE FOR MULTIPLE MYELOMA TREATMENT

CROSS-REFERENCE TO RELATED APPLICATIONS

This application is the National Stage of International Application No. PCT/GB2004/001062 filed on Mar. 12, 2004, which claims the benefit of U.S. Provisional Application No. 60/454,125, filed on Mar. 12, 2003 and U.S. Provisional Application No. 60/520,293, filed Nov. 14, 2003.

FIELD OF THE INVENTION

The present invention relates to the use of aplidine and analogues in the treatment of cancer, in particular in the treatment of multiple myeloma.

BACKGROUND OF THE INVENTION

Multiple myeloma represents a malignant proliferation of plasma cells derived from a single clone. The terms multiple myeloma and myeloma may be used interchangeably.

Plasma cells produce antibodies, proteins that move through the bloodstream to help the body get rid of harmful substances. Each type of plasma cell responds to only one specific substance by making a large amount of one kind of antibody. These antibodies find and act against that one substance. Because the body has many types of plasma cells, it can respond to many substances. When cancer involves plasma cells, the body keeps producing more and more of these cells. The unneeded plasma cells—all abnormal and all exactly alike—are called myeloma cells. Myeloma cells tend to collect in the bone marrow and in the hard outer part of bones. Sometimes they collect in only one bone and form a single mass, or tumor, called a plasmacytoma. In most cases, however, the myeloma cells collect in many bones, often forming many tumors and causing other problems. When this happens, the disease is called multiple myeloma (MM).

Because people with MM have an abnormally large number of identical plasma cells, they also have too much of one type of antibody. The tumor, its products, and the host response to it result in a number of organ dysfunctions and symptoms of bone pain or fracture, renal failure, susceptibility to infection, anemia, hypercalcemia, and occasionally clotting abnormalities, neurologic symptoms, and vascular manifestations of hyperviscosity.

MM is the 2nd most commonly diagnosed hematologic malignancy in the Western World, with an annual incidence of ~15,000 new cases in the U.S. alone. Unfortunately, MM is presently considered an incurable disease and the overall survival of MM patients has remained essentially unchanged at a median of 3-4 years, despite intense efforts over the last ~3 decades to improve on the activity of cytotoxic chemotherapy-based therapies for this disease. Importantly, the median age of diagnosis of MM in <65 years old and >⅓ of MM patients are <55 years old at diagnosis: for this substantial proportion of relatively young MM patients, the diagnosis of MM signifies, even in the absence of other co-morbidities, a high probability that their overall survival will be significantly shorter than the average life-expectancy of age-matched non-MM patients.

Recently, there have been a series of important advances in the therapeutic management of MM, namely the documentation of anti-MM activity of 2 new classes of anti-cancer agents, thalidomide (and its immunomodulatory derivatives) and the proteasome inhibitors. Although these classes of agents have been shown to be active in the setting of MM patients who were relapsed/refractory to conventional or high-dose cytotoxic chemotherapy-based regimens, a significant proportion of MM patients has de novo resistance to those novel agents, while initial responders (even those achieving durable complete remissions) can eventually relapse. Therefore the development of novel classes of anti-MM agents is urgently needed, in order to further improve the outcome of MM patients and, hopefully, to achieve high cure rates for this presently incurable neoplasia.

SUMMARY OF THE INVENTION

We have established for the first time that aplidine has very potent anti-multiple myeloma activity.

Aplidine (Dehydrodidemnin B) is a cyclic depsipeptide isolated from the Mediterranean tunicate *Aplidium albicans*.

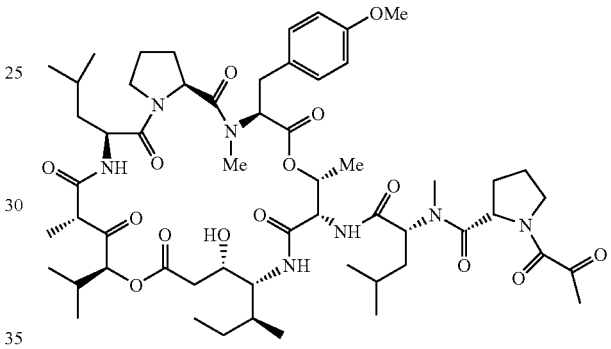

Aplidine

As used herein, the term aplidine also covers any pharmaceutically acceptable salt, ester, solvate, hydrate or a prodrug compound which, upon administration to the recipient is capable of providing (directly or indirectly) the compound aplidine. The preparation of salts and other derivatives, and prodrugs, can be carried out by methods known in the art.

Aplidine analogues include the compounds disclosed in WO 02/2596.

More information on aplidine, aplidine analogues, their uses, formulations and synthesis can be found in patent applications: WO 91/9485, WO 98/1352, WO 99/42125, WO 01 76616, WO 01/35974, WO 02/30441 and WO 02/2596. We incorporate by specific reference the content of each of these PCT texts.

Aplidine has been shown, both in vitro and in clinical phase I and II trials to have potential of being useful as an anticancer agent. Aplidine has several modes of action, including the blockade of VEGF secretion, inhibition of protein synthesis and signal transduction, and inducing G1 cell cycle arrest. The dose-limiting toxicity in phase I/II trials was muscular toxicity, with a remarkable lack of severe myelosuppression.

Aplidine shows potent in vitro activity against human tumor solid cell lines, especially non-small-cell lung and colon tumor cells with $IC_{50}$ values at 0.18 nM and 0.45 nM respectively (Faircloth et al., 1995, *Proceedings 8<sup>th</sup> ECCO Congress, Paris*, Abstract no. 122, 529; Lobo et al., 1997, Anticancer Res, 17, 333-336). The National Cancer Institute's (NCI) human in vitro panel has confirmed selectivity for non-small-cell lung cancer (NSCLC), melanoma, ovarian and colorectal cancer cell lines (Faircloth et al., 1996, Ann Oncol., 7, 34).

Initial studies with this marine depsipeptide suggested in vivo activity against murine tumors such as B16 melanoma (Faircloth et al., 1995, Proceedings 8th ECCO Congress, Paris, Abstract no. 122, 529). Moreover, additional in vivo studies performed in mice bearing human xenografted tumors confirm activity against breast MX-1 and colon CX-1 (Faircloth et al., 1996, Ann Oncol., 7, 34). A phase I trial in pediatric leukemia is under implementation (Jimeno J. et al., 2002, Ann Oncol., 13 (suppl. 5), Abst. 65P). Finally, it has been shown that aplidine also demonstrated in vivo antitumor activity against subcutaneous implanted gastric, prostate and Burkitts lymphoma human xenografts as well as bladder carcinoma in the hollow fiber (Faircloth et al., 1999, Proc. Am. Assoc. Cancer Res., 40, Abstract 2612; Faircloth et al., 1998, Proc. Am. Assoc. Cancer Res., 39, Abstract 227).

The present invention is directed to the use of aplidine and analogues in the treatment of multiple myeloma.

The present invention is also directed to a pharmaceutical composition comprising aplidine or an analogue and a pharmaceutically acceptable carrier, vehicle or diluent, to be used in the treatment of multiple myeloma.

The present invention further provides a method of treating any mammal, notably a human, affected by multiple myeloma which comprises administering to the affected individual a therapeutically effective amount of aplidine or an analogue.

In another aspect the present invention is directed to the use of aplidine or an analogue in the manufacture of a medicament for the treatment of multiple myeloma.

The invention additionally provides kits comprising separate containers containing a pharmaceutical composition comprising aplidine or an analogue, and a reconstituting agent. Methods of reconstitution are also provided.

DETAILED DESCRIPTION OF THE INVENTION

Figure 1:
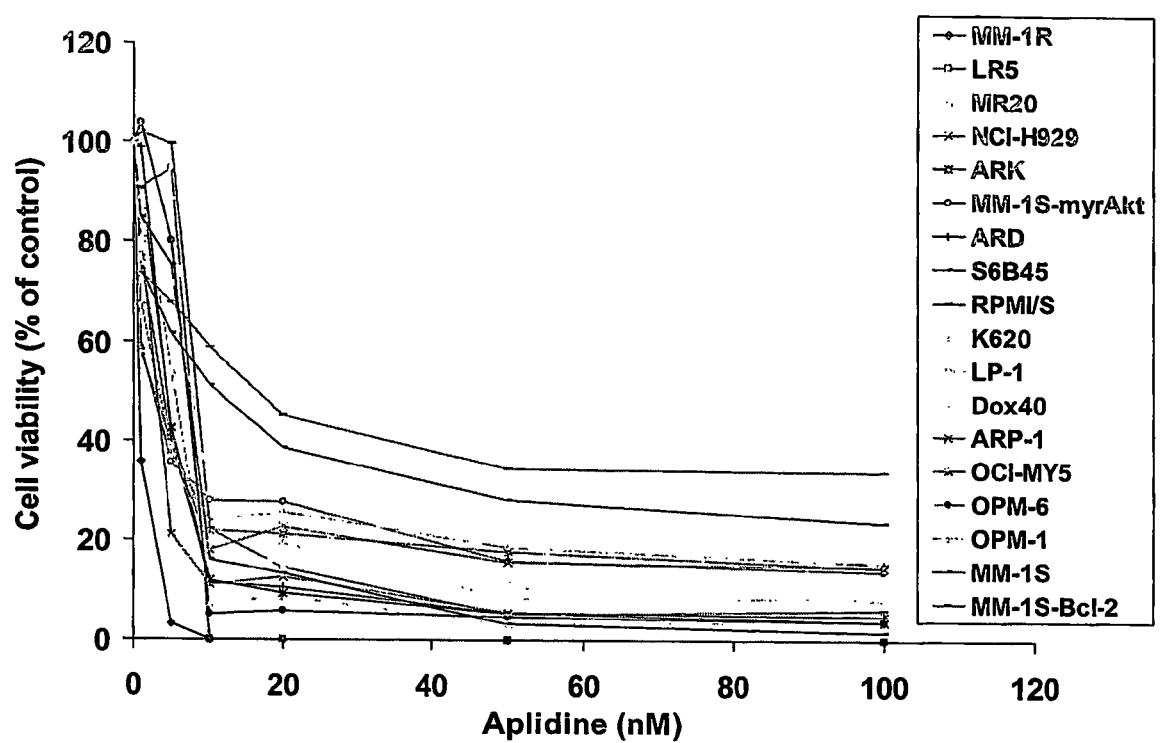
FIG. 1. Results of MTT colorimetric survival assays of a panel of aplidine-treated MM cell lines FIG. 2. Aplidine (20 nM for 48 hrs) in vitro activity against primary MM tumor cell samples derived from multi-drug resistant MM patients FIG. 3. Co-culture of primary MM tumor cells (isolated from multi-drug resistant MM patients) with bone marrow stromal cells (BMSCs) does not significantly attenuate the responsiveness of MM cells to Aplidin FIG. 4. A) Aplidine treatment (20 nM, 0-12 hrs) of primary MM tumor cells from a multi-drug resistant MM patient suppresses the secretion of VEGF FIG. 4. B) Aplidine (20 nM, 12 hrs) suppresses the VEGF secretion by primary MM tumor cells, BMSCs, as well as by co-cultured MM cells and BMSCs FIG. 5. Aplidine sensitizes primary MM tumor cells to doxorubicin FIG. 6. Aplidine inhibits growth of dexamethasone resistant multiple myeloma (MM1.R) cells in culture as effectively as the parenteral line (MM1.S)

Despite recent advances in the therapeutic management of multiple myeloma (MM), no curative therapy currently exists for this disease, which is the $2^{nd}$ most commonly diagnosed hematologic malignancy in the Western World. The identification of novel therapeutic agents with anti-MM activity, especially in patients who relapse or do not optimally respond to conventional and/or novel therapies remains an urgent priority.

We found that Aplidine (APL), a new marine-derived depsipeptide, is very potent against MM cells in vitro. Specifically, we observed that clinically relevant concentrations of APL were active against a broad panel of human MM cell lines, which included MM cell lines resistant to conventional anti-MM agents (e.g. dexamethasone, alkylating agents, anthracyclines) or novel anti-MM agents (e.g. thalidomide, immunomodulatory thalidomide derivatives, proteasome inhibitor PS-341[bortezomib], Apo2L/TRAIL), or cells over-expressing major anti-apoptotic regulators for MM cells. MTT calorimetric survival assays showed that aplidine was universally active against the cell lines of our panel, with $IC_{50}$ doses (for the overwhelming majority of these MM cell lines) in the range of 10 nM or less. Importantly, this potent in vitro anti-MM activity was triggered by concentrations of APL which were clinically achievable in the phase I clinical trial of this agent in solid tumors. Furthermore these $IC_{50}$ values were comparable with the in vitro activity of this agent in the most APL-sensitive solid tumor models.

To further confirm that the in vitro anti-MM activity of APL is not restricted to only cell line models, we also tested the effect of APL against primary MM tumor cells freshly isolated from patients resistant to thalidomide or its analogs and/or proteasome inhibition. In a preliminary testing of 10 primary tumor specimens from MM patients (>90% purity for CD138+ CD38+ MM tumor cells), we observed in vitro anti-MM activity of aplidine consistent with the results obtained from the testing of our cell line panel. Taken together, the results of in vitro studies of aplidine against primary MM tumor specimens and MM cell lines indicate that this agent can be active against a broad spectrum of MM cells, including those with de novo or acquired resistance to conventional therapies or other novel agents with potent anti-MM activity.

Although cytoline- or cell adhesion-mediated interactions of the local bone marrow (BM) microenvironment (e.g. BM stromal cells) protects MM cells from conventional therapies (e.g. dexamethasone or cytotoxic chemotherapy) (refs), APL is able to overcome this protective effect in co-culture models of MM cells with BM stromal cells.

In addition, APL sensitized MM cells to cytotoxic chemotherapy-induced cell death and abrogated secretion of pro-angiogenic cytokines (e.g. VEGF) by MM cells or BM stromal cells in ex vivo co-culture models. This suggest that aplidine can be combined with conventional cytotoxic chemotherapy-based protocols to achieve increased anti-MM activity. Comparative analyses of the patterns of MM cell sensitivity to APL vs. other anti-cancer drugs showed that the dose-response relationship of MM treated with APL is distinct from those associated with administration of drugs. This further supports the notion that the anti-MM properties of APL are mediated by molecular mechanisms distinct from those of currently available anti-MM drugs, and also suggests that APL may be active even against subgroups of MM which could be resistant to other novel therapies which are currently in clinical development. These findings coupled with the favourable safety profile of APL in clinical trials for solid tumors.

For the present invention, analogues of aplidine can be used in place of APL, aplidine itself. Typically such compounds are as defined in WO 0202596. Examples of compounds for the present invention include the preferred compounds given in WO 0202596, and in particular we import into this patent specification the discussion of preferred compounds and related aspects given in WO 0202596. More preferably, the analogues are structurally close to aplidine, and usually differ from aplidine in respect of one amino acid or the terminal sidechain. The different amino acid can be in the cyclic part of the molecule or in the sidechain. Many examples of such compounds are given in WO 0202596, and they are candidates for use in the present invention.

Pharmaceutical formulations of aplidine or analogues may be adapted for administration by any appropriate route, for example by the oral (including buccal or sublingual), rectal, nasal, topical (including buccal, sublingual or transdermal), vaginal or parenteral (including subcutaneous, intramuscular, intravenous or intradermal) route. Such formulations may be prepared by any method known in the art of pharmacy, for example by bringing into association the active ingredient with the carrier(s) or excipient(s).

Examples of pharmaceutical compositions containing aplidine or analogues include liquid (solutions, suspensions or emulsions) with suitable composition for intravenous administration, and they may contain the pure compound or in combination with any carrier or other pharmacologically active compounds. Solubilised aplidine shows substantial degradation under heat and light stress testing conditions, and a lyophilised dosage form was developed, see WO 99/42125 incorporated herein by reference.

Administration of aplidine and analogues or compositions of the present invention can be by intravenous infusion. Infusion times of up to 72 hours can be used, more preferably 1 to 24 hours, with either about 1, about 3 or about 24 hours most preferred. Short infusion times which allow treatment to be carried out without an overnight stay in hospital are especially desirable. However, infusion may be around 24 hours or even longer if required. Infusion may be carried out at suitable intervals with varying patterns, illustratively once a week, twice a week, or more frequently per week, repeated each week optionally with gaps of typically one week.

In the preferred application method, the administration is performed in cycles. An intravenous infusion of a compound of the invention is given to the patients the first week of each cycle, the patients are allowed to recover for the remainder of the cycle. The preferred duration of each cycle is of either 1, 3 or 4 weeks; multiple cycles can be given as needed. In an alternative dosing protocol, the compound of the invention is administered for say about 1 hour for 5 consecutive days every 3 weeks. Other protocols can be devised as variations.

Dose delays and/or dose reductions and schedule adjustments are performed as needed depending on individual patient tolerance of treatments.

Although guidance for the dosage is given above, the correct dosage of the compound may change according to the particular formulation, the mode of application, and the particular situs, host and tumour being treated. Other factors like age, body weight, sex, diet, time of administration, rate of excretion, condition of the host, drug combinations, reaction sensitivities and severity of the disease shall be taken into account. Administration can be carried out continuously or periodically within the maximum tolerated dose. Further guidance for the administration of aplidine is given in WO 01/35974 which is incorporated herein by reference in its entirety.

Aplidine and analogues may be used with other drugs to provide a combination therapy in the treatment of multiple myeloma. The other drugs may form part of the same composition, or be provided as a separate composition for administration at the same time or at different time.

EXAMPLES

Statistical Analysis

Statistical significance was examined by a 2-way analysis of variance, followed by Duncan post hoc test. In all analyses, $P<0.05$ was considered statistically significant.

Example 1

MTT Calorimetric Survival Assay

Cell survival was examined using the 3-(4,5-dimethylthiazol-2-yl)-2,5-diphenyltetrazolium bromide (MTT; Sigma Chemical, St Louis, Mo.) colorimetric assay, as previously described (Mitsiades C. S. et al. *Blood.* 2001, 98, 795-804; Mitsiades N. et al. *Proc Natl Acad Sci USA.* 2002, 99, 14374-14379; Mitsiades N. et al. *Blood.* 2003, 101, 2377-2380). Briefly, cells were plated in 48-well plates at 70% to 80% confluence in the presence of 2.5% fetal bovine serum (FBS) and in the presence of Aplidine at final concentration of 0-100 nM or DMSO vehicle control. At the end of each treatment, cells were incubated with 1 mg/mL MTT for 4 hours at 37° C.; a mixture of isopropanol and 1 N HCl (23:2, vol/vol) was then added under vigorous pipetting to dissolve the formazan crystals. Dye absorbance (A) in viable cells was measured at 570 nm, with 630 nm as a reference wavelength. Cell viability was estimated as a percentage of the value of untreated controls. All experiments were repeated at least 3 times, and each experimental condition was repeated at least in triplicate wells in each experiment. Data reported are average values±SD of representative experiments.

Panel of Drug-resistant MM Cell Lines and Primary MM Tumor Cells

We evaluated the activity of aplidine in a panel of drug-sensitive and drug-resistant human MM cell lines, which included the following cell lines: the dexamethasone (Dex)-sensitive MM-1S and Dex-resistant MM-1R cell lines (kindly provided as an academic gift by Dr Steven Rosen, Northwestern University, Chicago, Ill.); the chemo-sensitive RPMI-8226/S cell line and their doxorubicin-(Dox6, Dox40), melphalan (LR5)-, and mitoxantrone (MR20)-resistant sublines (kindly provided as an academic gift by Dr William Dalton, Lee Moffitt Cancer Center, Tampa, Fla.); OCI-My-5 cells by Dr H. A. Messner (Ontario Cancer Institute, ON, Canada); S6B45 cells by Dr T. Kishimoto (Osaka University, Osaka, Japan); ARD, ARK and ARP-1 cells (kindly provided by Dr Nikhil Munshi, Dana-Farber Cancer Institute, Boston, Mass.); the OPM-1, OPM-6, K620 and LP-1 cells (kindly provided as an academic gift by Dr Leif Bergsagel, Cornell University, New York, N.Y.); as well as U266 and NCI-H929 cells obtained from the American Type Culture Collection (Rockville, Md.).

Primary MM tumor cells were isolated from bone marrow (BM) aspirates of 10 patients, who were resistant to conventional (steroid- and cytotoxic chemotherapy-based) and more recently developed anti-MM agents (e.g. thalidomide or proteasome inhibitors). The BM aspirates were initially processed by Ficoll density centrifugation, purified by CD138+ selection (either by flow cytometry activated cell sorting (FACS), or by CD138+ positive selection with immunomagnetic separation), using previously described protocols (Mitsiades C. S. et al *Blood.* 2001, 98, 795-804). All sorted tumor cell samples had >90% purity in CD38+ CD138+ or CD38+ CD45RA− cells. Immediately prior to Aplidine treatment, all primary tumor samples were confirmed to have more than 95% viability, by trypan blue exclusion assay. All MM cell lines and patient MM cells were cultured in RPMI 1640 medium (Gibco Laboratories, Grand Island, N.Y.) supplemented with 10% charcoal dextran-treated fetal bovine serum (FBS; Hyclone, Logan, Utah) as well as L-glutamine, penicillin, and streptomycin (Gibco Laboratories).

Results: Activity of Aplidine Against Drug-resistant MM Cell Lines and Primary Tumor Specimens We tested the in vitro activity of aplidine against a broad panel of human MM cell lines, which included MM cells sensitive or resistant to conventional (e.g. dexamethasone, alkylating agents, anthracyclines) or novel (e.g. thalidomide, immunomodulatory thalidomide derivatives, Apo2L/TRAIL) anti-MM agents. MTT calorimetric survival assays (FIG. 1) showed that Aplidine was universally active against the cell lines of our panel, with $IC_{50}$ doses (for the overwhelming majority of these MM cell lines) in the range of 10 nM or less (which corresponds to clinically achievable concentrations of aplidine, based on the phase I trial experience with this agent). Importantly, this in vitro activity of aplidine is comparable with its in vitro activity in the most aplidine-sensitive solid tumor models. Using hierarchical clustering analyses and relevance network algorithms, we compared the patterns of MM cell sensitivity to aplidine vs. other anti-cancer drugs and found that the pattern of dose-response relationships for aplidine is clearly distinct from those for other drugs.

This finding not only further supports the notion that the anti-MM properties of aplidine are mediated by molecular mechanisms distinct from those of other drugs, but also suggests that APL may be active even against different molecular subgroups of this disease.

Results: Activity of Aplidine Against Drug-resistant Primary MM Tumor Cells

Figure 2:
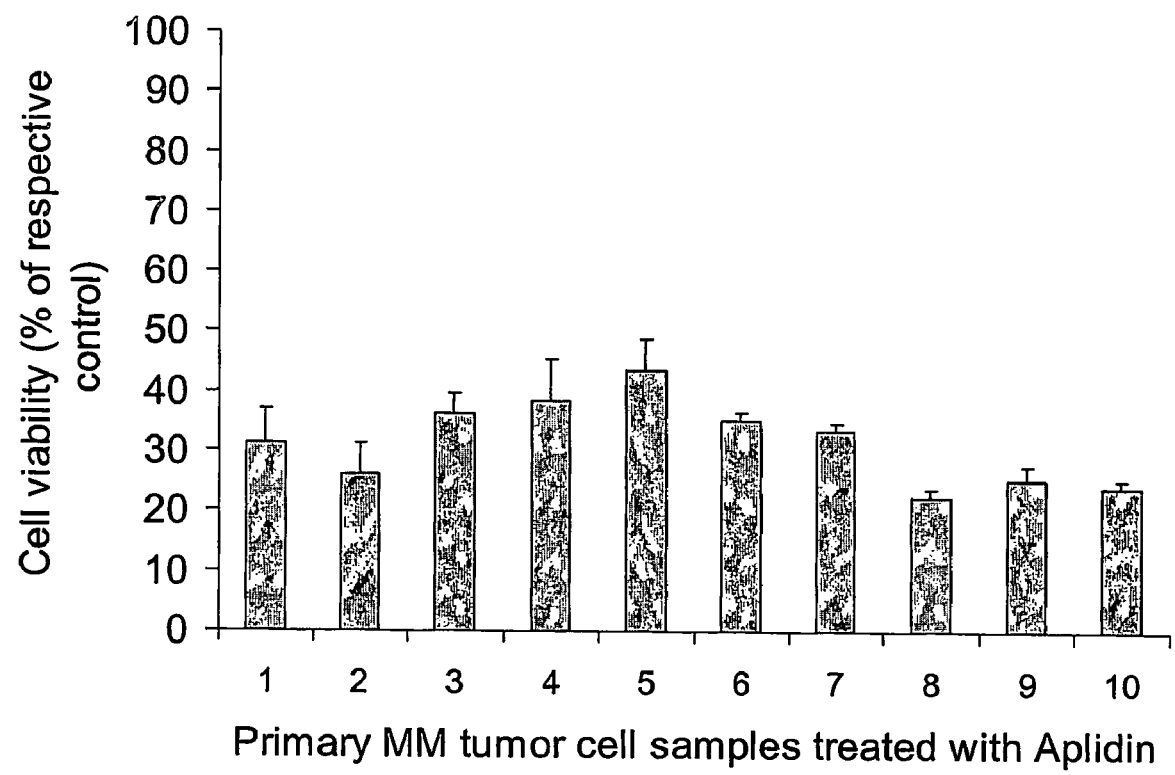

To further confirm that the in vitro anti-MM activity of APL is not restricted to only cell line models, we also tested the effect of APL against primary MM tumor cells freshly isolated from patients resistant to thalidomide or its analogs and/or proteasome inhibition. In a preliminary testing of 10 primary tumor specimens from MM patients (>90% purity for CD138+ CD38+ MM tumor cells), we observed in vitro anti-MM activity of Aplidine consistent with the results obtained from the testing of our cell line panel (FIG. 2).

Taken together, the results of in vitro studies of aplidine against primary MM tumor specimens and MM cell lines indicate that this agent can be active against a broad spectrum of MM cells, including those with de novo or acquired resistance to conventional therapies or other investigational agents with potent anti-MM activity.

Example 2

Stable Transfections of Bcl-2 and Constitutively Active Akt

MM-1S cells were stably transfected with plasmid vector encoding myristoylated (constitutively active) Akt or Bcl-2 (Upstate Biotechnologies, Lake Placid, N.Y.) or with empty (neo) vectors, and were performed using Lipofectamine 2000 (Life Technologies), followed by cultures in G418-containing selection media, as previously described (Mitsiades C. S. et al. *Oncogene.* 2002, 21, 5673-5683; Mitsiades N. et al. *Proc Natl Acad Sci USA.* 2002, 99, 14374-14379).

Results: Aplidine Overcomes the Anti-apoptotic Effect of Bcl-2 or Constitutively Active Akt Because of the roles of Bcl-2 and the PI-3K/Akt cascade in the regulation of drug-induced apoptosis in MM and other neoplasias, we also characterized the activity of aplidine in MM-1S human MM cells stably transfected with Bcl-2 or myristoylated Akt constructs vs. empty vector-transfected control MM-1S cells. We observed that Bcl-2- or myrAkt-transfected cells did not have lower sensitivity to aplidine than empty-vector transfected cells (FIG. 1), suggesting that overexpression of Bcl-2 or constitutive activation of Akt and its downstream effectors are not sufficient to overcome the anti-MM effect of aplidine.

Example 3

Co-Culture Assays of MM Cells with Bone Marrow Stromal Cells (BMSCs)

When adhering to BMSCs, MM cells have reduced sensitivity to conventional anti-MM therapies, such as dexamethasone or cytotoxic chemotherapeutics (Chauhan D. et al. *Blood.* 1996, 87, 1104-1112). This form of drug resistance is considered a key reason why MM patients eventually relapse when they receive treatment based on administration of glucocorticoids and/or cytotoxic chemotherapy. In contrast, among recently developed therapies for MM, anti-tumor activity against in cases of chemo-resistant or steroid-resistant MM has been achieved by classes of drugs, e.g. proteasome inhibitors (Hideshima T. et al. *Cancer Res.* 2001, 61, 3071-3076), which can overcome the protective effects of BMSCs on MM cells. We therefore investigated whether aplidine can also overcome the molecular sequelae of the interaction of BMSCs with MM cells and achieve anti-MM activity in this context. We thus performed in vitro co-culture assays of MM cells with BMSCs as previously described: BMSCs were grown on 24-well plates to confluency. Following washings with serum-free medium, primary tumor cells (>95% purity in CD138+ cells) isolated from 3 MM patients were added to BMSC-coated or control wells as described previously (Uchiyama H. et al. *Blood.* 1993, 82, 3712-3720; Mitsiades N. et al. *Blood.* 2003, 101, 4055-4062) and incubated for 48 hours in the presence or absence of aplidine. Flow cytometric analysis was performed to detect the CD138+ population of viable MM cells and the effect of aplidine on MM cell viability was expressed as % of viable cell numbers in comparison to the respective vehicle-treated cultures.

Figure 3:
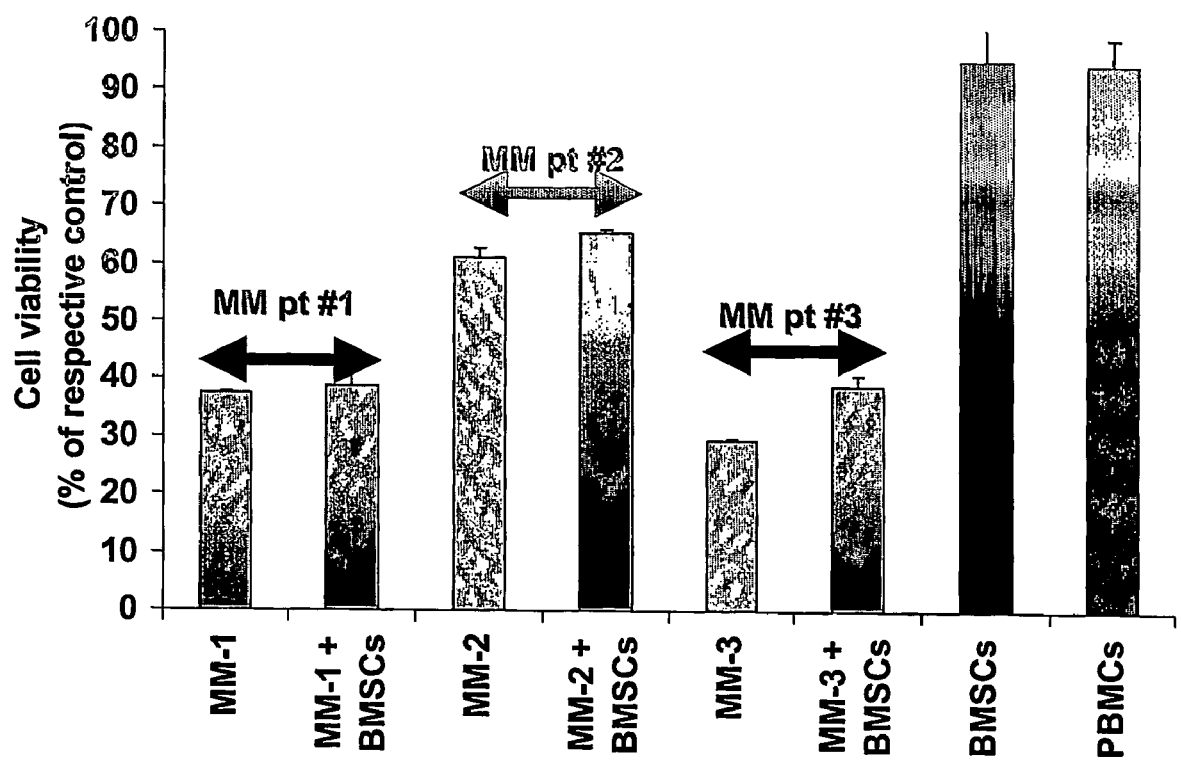

Results: Aplidine Overcomes the Protective Effect of Bone Marrow Stromal Cells (BMSCs) on MM Cells Previous studies from our group and other investigators have shown that cytokine- or cell adhesion-mediated interactions of the local bone marrow (BM) microenvironment (e.g. BM stromal cells) can protect MM cells from conventional therapies (e.g. dexamethasone or cytotoxic chemotherapy) (Chauhan D. et al. *Blood.* 1996, 87, 1104-1112). We thus evaluated the anti-MM effect of Aplidine in the setting of co-culture of MM cells with BMSCs and observed, using flow-cytometric determination of cell death in the MM cell compartment (FIG. 3), that the MM-BMSC interaction did not significantly attenuate the in vitro anti-MM activity of aplidine (at aplidine doses which did not significantly affect the survival of BMSCs).

Example 4

Quantification of VEGF Secretion

MM cell adhesion to BMSCs induces increased secretion of angiogenic cytokines, such as vascular endothelial growth factor (VEGF), an event deemed of major significance for the recruitment of new blood vessels at the sites of MM cells in the BM milieu. We therefore evaluated whether aplidine can suppress the secretion of VEGF by MM and/or BMSCs using the previously described in vitro co-culture assays of MM cells with BMSCs: BMSCs were grown on 24-well plates to confluency. Following washings with serum-free medium, primary tumor cells (>95% purity in CD138$^+$ cells) isolated from 3 MM patients were added to BMSC-coated or control wells as described previously (Uchiyama H. et al. *Blood.* 1993, 82, 3712-3720; Mitsiades N. et al. *Blood.* 2003, 101, 4055-4062) and incubated for 12 hours in the presence or absence of Aplidine. The supernatants were collected and assayed for VEGF concentration by enzyme-linked immunosorbent assay (ELISA) using a commercially available kit (VEGF ELISA kit; R&D Systems), according to the instructions of the manufacturer.

Results: Aplidine Decreases the Secretion of VEGF by MM/BMSCs

Figure 4:
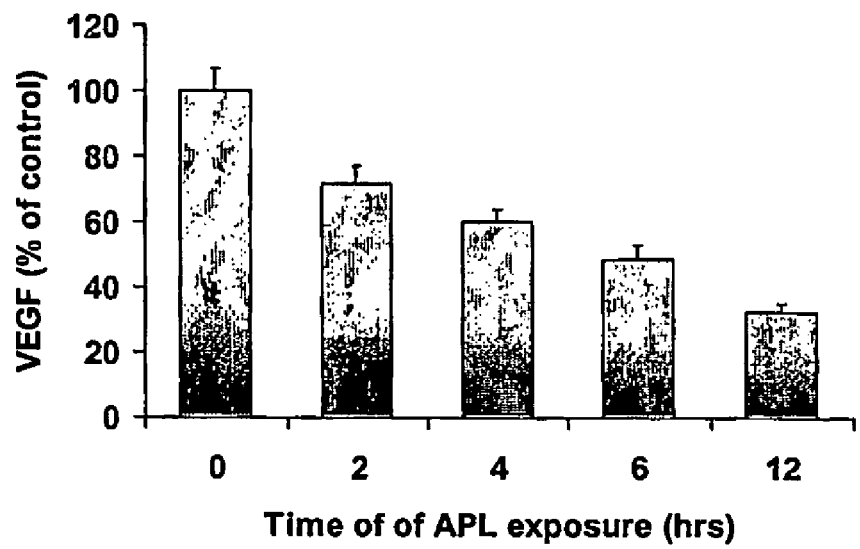
Figure 4:
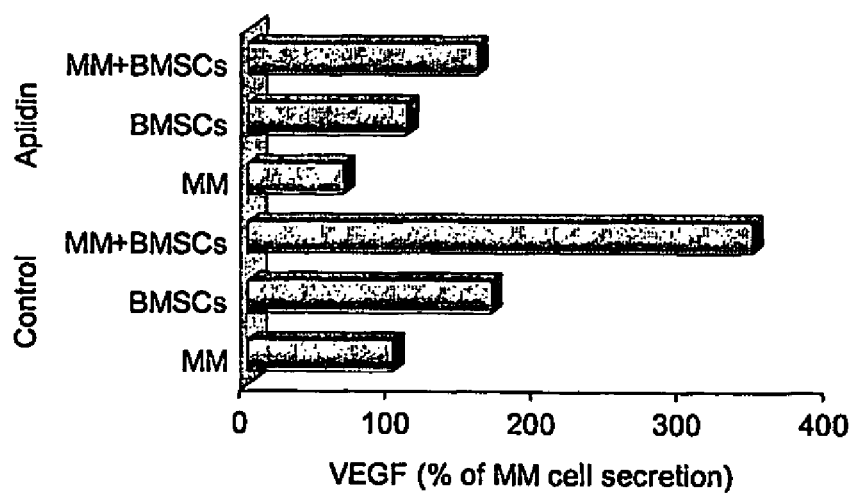

VEGF has been proposed as a putative mediator of proliferative responses for MM cells in the BM microenvironment. VEGF is also a key mediator of tumor-induced recruitment of new blood vessels in the areas of tumor cell growth. Because of preliminary reports suggesting that aplidine treatment of acute leukemic cells leads to suppression of VEGF secretion, we studied whether Aplidine can also suppress the secretion of VEGF by MM cells and/or by BMSCs. Indeed, a 12-hour treatment with aplidine (20 nM) was able to suppress the secretion of VEGF by MM cells, as well as counteract the increase in VEGF secretion which occurs when MM cells are co-cultured with BMSCs (FIGS. 4A and 4B).

Example 5

Results: Aplidine Sensitizes MM Cells to Cytotoxic Chemotherapeutics

Figure 5:
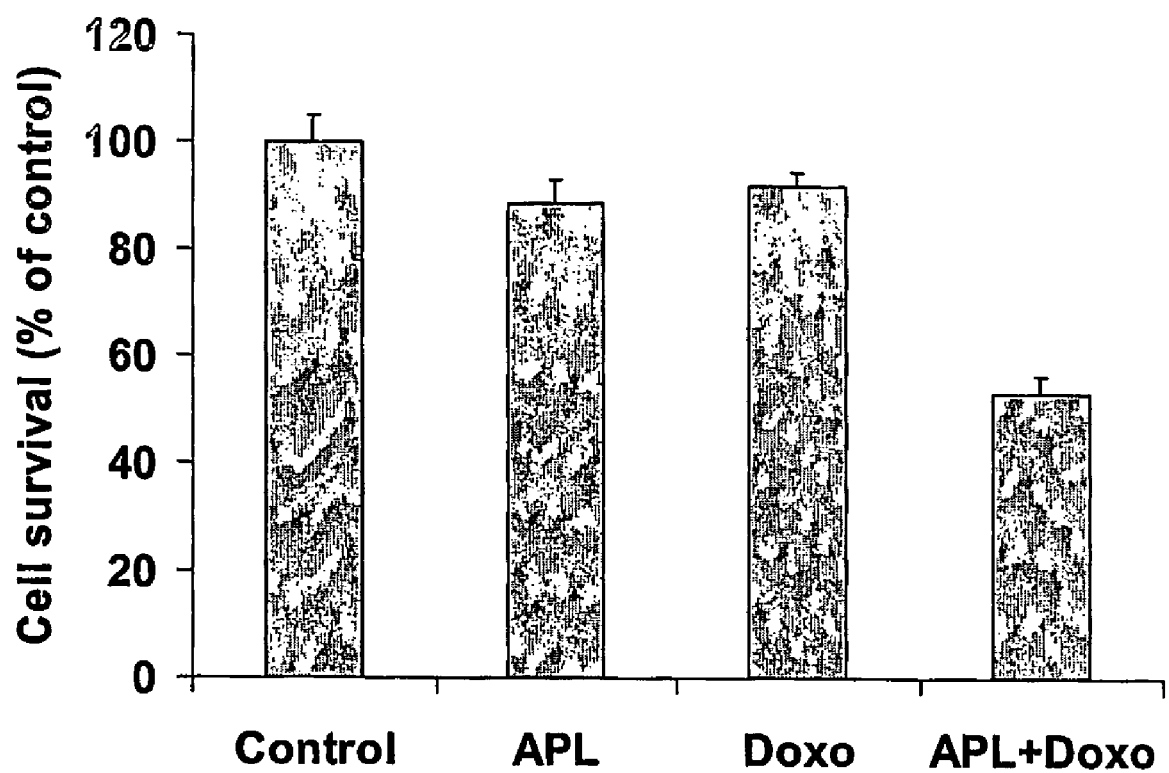

Using MTT calorimetric survival assays we found that MM cells have increased responsiveness to doxorubicin when this treatment is combine with Aplidine. FIG. 5 illustrates the example of a primary MM tumor sample sensitized to with doxorubicin (10 ng/mL) by treatment with aplidine (2 nM).

Example 6

Aplidine was tested against various established cells in culture. The cells used were:
multiple myeloma cells (MM1.S)
multiple myeloma lines resistant to dexamethasone (MM 1.R)
a multiple myeloma line overexpressing Bcl-2

For established cell lines, cells were plated in 96 well plates and allowed to grow for 24 h prior to addition of drugs. Cells were incubated with drug for indicated times and cell viability was measured by the XTT or MTS assay using an automated plate reader.

Figure 6:
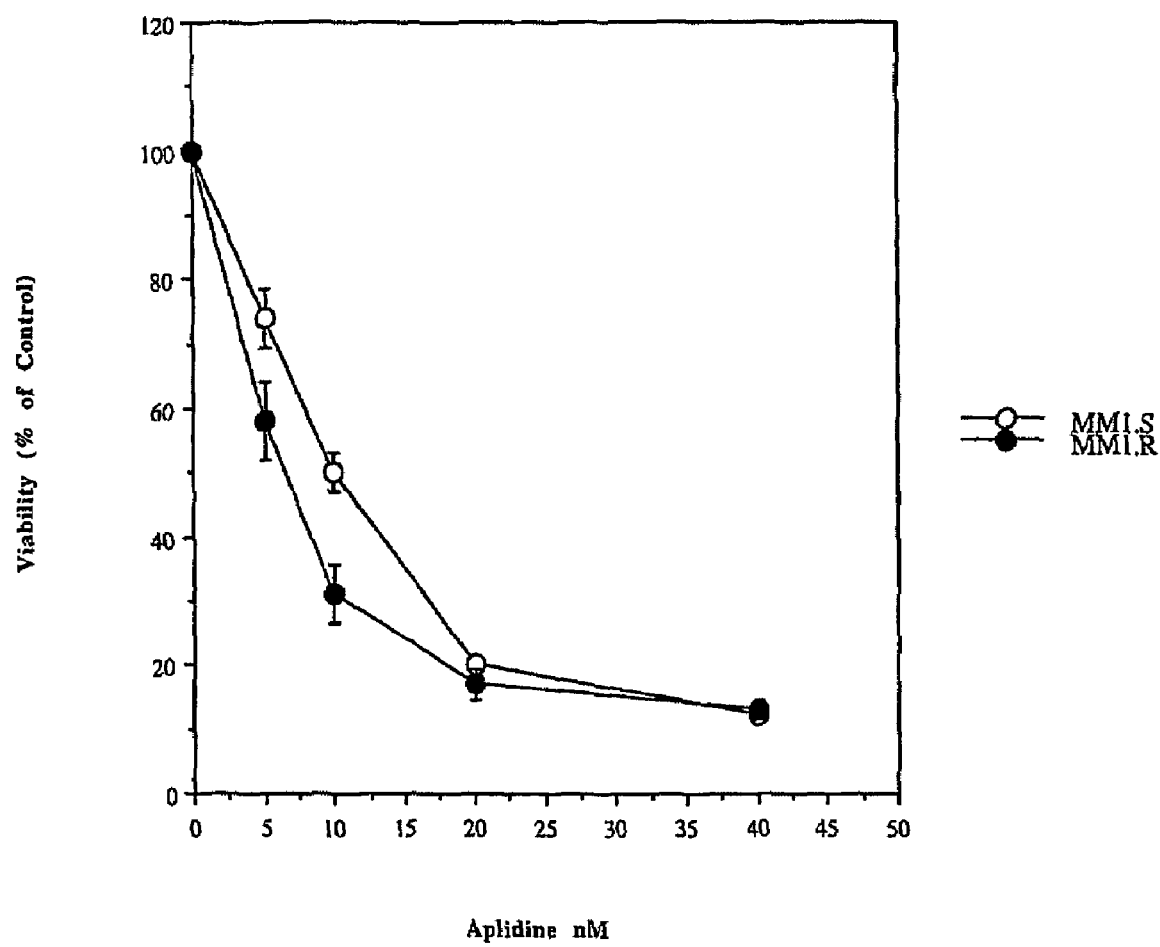
Figure 7:
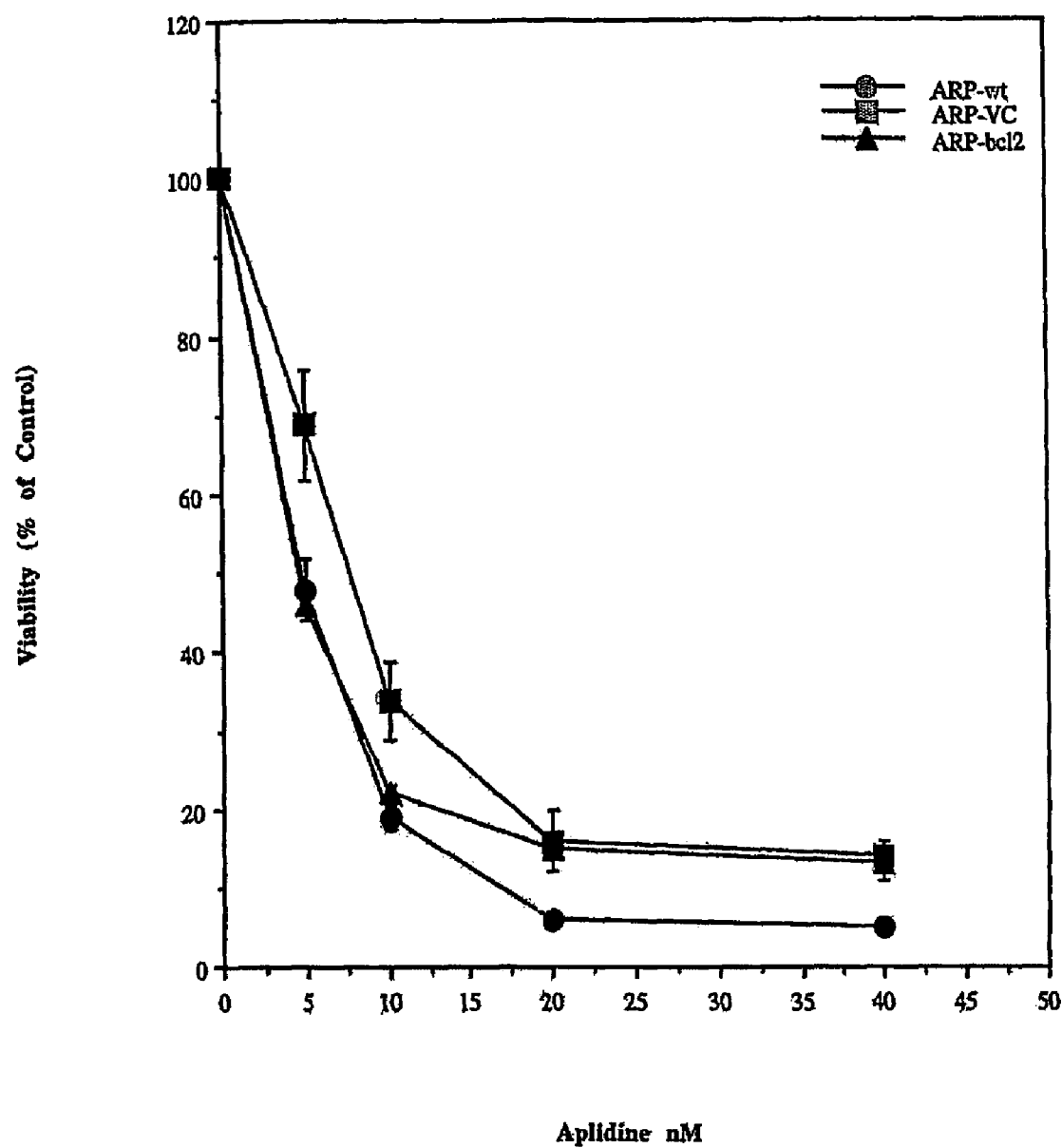
FIG. 7. Aplidine inhibits growth of Bcl-2 overexpressing MMcells

The results of these studies are shown in FIGS. 6-7.

The invention claimed is:

1. A method for treating any mammal affected by multiple myeloma which comprises administering to the affected mammal a therapeutically effective amount of aplidine.

2. The method according to claim 1, wherein aplidine is used in combination with other drug or drugs to provide a combination therapy.

3. The method of claim 1, wherein the mammal is a human.

* * * * *